US011291596B2

(12) United States Patent
Suyama

(10) Patent No.: US 11,291,596 B2
(45) Date of Patent: Apr. 5, 2022

(54) ABSORBENT PAD

(71) Applicant: DAIO PAPER CORPORATION, Ehime (JP)

(72) Inventor: Junnosuke Suyama, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 322 days.

(21) Appl. No.: 16/493,016

(22) PCT Filed: Mar. 6, 2018

(86) PCT No.: PCT/JP2018/008474
§ 371 (c)(1),
(2) Date: Sep. 11, 2019

(87) PCT Pub. No.: WO2018/173737
PCT Pub. Date: Sep. 27, 2018

(65) Prior Publication Data
US 2020/0060894 A1 Feb. 27, 2020

(30) Foreign Application Priority Data
Mar. 21, 2017 (JP) .............................. JP2017-055039

(51) Int. Cl.
*A61F 13/534* (2006.01)
*A61F 13/494* (2006.01)
(Continued)

(52) U.S. Cl.
CPC .. *A61F 13/53409* (2013.01); *A61F 13/49406* (2013.01); *A61F 13/5323* (2013.01);
(Continued)

(58) Field of Classification Search
CPC ............ A61F 13/5323; A61F 13/53409; A61F 2013/530481; A61F 2013/530985; A61F 2013/5307; A61F 2013/53054
See application file for complete search history.

(56) References Cited

U.S. PATENT DOCUMENTS

| | | | |
|---|---|---|---|
| 6,646,180 B1* | 11/2003 | Chmielewski | .... A61F 13/15658 428/220 |
| 2015/0245958 A1* | 9/2015 | Chmielewski | ........ A61F 13/535 604/385.201 |

FOREIGN PATENT DOCUMENTS

| | | |
|---|---|---|
| EP | 0 481 322 A1 | 4/1992 |
| JP | H0549658 A | 3/1993 |

(Continued)

OTHER PUBLICATIONS

Translation of International Search Report dated Apr. 24, 2018 and Written Opinion of corresponding application No. PCT/JP2018/008474; 9 pgs.

(Continued)

*Primary Examiner* — Susan S Su
(74) *Attorney, Agent, or Firm* — Maier & Maier, PLLC

(57) ABSTRACT

Provided is an absorbent pad which prevents leakage of excess liquid excrement to the exterior. An absorbent pad sheet forms an absorbent pad from a liquid-permeable front sheet and a liquid permeable rear sheet, and absorbent polymer particles which absorb liquid excrement and which are provided between the front sheet and the rear sheet. The width in the width direction formed between both side parts folded to the inside is formed as 10-50% of the width of the absorbent pad in the width direction, and some of the absorbent polymer particles at the place at which folding to the inside occurs are made to penetrate the front sheet at the place at which folding to the inside occurs.

11 Claims, 11 Drawing Sheets

(51) Int. Cl.
*A61F 13/53* (2006.01)
*A61F 13/532* (2006.01)

(52) U.S. Cl.
CPC ............... *A61F 2013/5307* (2013.01); *A61F 2013/53054* (2013.01); *A61F 2013/530985* (2013.01)

(56) References Cited

FOREIGN PATENT DOCUMENTS

| | | |
|---|---|---|
| JP | 2004-500165 A | 1/2004 |
| JP | 2006-297073 A | 11/2006 |
| JP | 2013-132460 A | 7/2013 |
| JP | 2016-526983 A | 9/2016 |
| WO | 2013/094726 A1 | 6/2013 |

OTHER PUBLICATIONS

Extended European Search Report dated Feb. 19, 2020, in connection with corresponding EP Application No. 18770445.7; 6 pages.
Chinese Office Action dated Mar. 10, 2021, in connection with corresponding CN Application No. 201880019104.3 (12 pp., including machine-generated English translation).
Japanese Office Action dated May 16, 2018, in connection with corresponding JP Application No. 2017-055039 (6 pp., including machine-generated English translation).

\* cited by examiner

ABSORBENT PAD

FIELD

The present invention relates to absorbent pads used for absorbent articles such as disposable diapers and sanitary napkins and pads.

BACKGROUND

Traditionally, a prior art proposes a technique of forming an absorbent pad by using a liquid-permeable front sheet, a liquid-permeable rear sheet and absorbent polymers in between the front sheet and the liquid-permeable rear sheet and by folding the both ends of the width direction of the absorbent pad sheet inward. (Patent Document 1)

Another prior art proposes a technique of forming an absorbent pad by using a liquid-permeable front sheet, a liquid-permeable rear sheet and absorbent polymers and pulp fibers in between the front sheet and the liquid-permeable rear sheet, by folding the both ends of the width direction of the absorbent pad sheet inward and further, by folding the inside of the folded both ends outward. (Patent Document 2)

[Patent Document 1] Japanese Unexamined Patent Publication No. 2004-500165
[Patent Document 2] Japanese Unexamined Patent Publication No. 2013-132460

SUMMARY OF INVENTION

However, according to the technique of Patent Document 1, there is a risk of leaking the excess liquid excretions that did not absorb into the absorbent pad to outside since the spacing formed in between the folded both ends inward is formed in a slit configuration.

Further, according to the technique of Patent Document 2, the thickness of the absorbent pad is thick because of the formation by folding and therefore, it may give discomforts to a wearer.

In view of the foregoing, the subject of the invention is to provide an absorbent pad that prevents the leakage of the excess liquid excretions not being absorbed by the absorbent pad to outside.

The subject of the invention has been achieved and disclosed as the following: A first aspect of the present invention is directed to an absorbent pad formed by folding the both ends of the width direction of an absorbent pad sheet inward, the absorbent pad sheet is formed with a liquid-permeable front sheet, a liquid-permeable rear sheet and absorbent polymer particles absorbing the liquid excretions that are provided in between the liquid-permeable front sheet and the liquid-permeable rear sheet, the width in the width direction formed between the both ends folded inward is formed 10 to 50% with respect to the width in the width direction of the absorbent pad, and a part of the absorbent polymer particles in the sections folded inward is passed to the inside of the front sheet in the sections folded inward.

A second aspect of the present invention is, as in the embodiment of the first aspect, the front sheet and the rear sheet are connected with first junctions extending in the longitudinal direction at predetermined intervals in the width direction and second junctions extending in the width direction at predetermined intervals in the longitudinal direction and the absorbent polymer particles are packed within plurality of cells defined by the first junctions and the second junctions when viewed in plan.

A third aspect of the present invention is, as in the embodiment of the first aspect or the second aspect, the base weight of the front sheet is greater than the base weight of the rear sheet.

A fourth aspect of the present invention is, as in the embodiment of any one of the first, second or third aspect, the thickness of the front sheet is formed thicker than the thickness of the rear sheet.

A fifth aspect of the present invention is, as in the embodiment of any one of the first, second, third or fourth aspect, the base weight of the absorbent polymer particles in the sections folded inward is arranged greater than the base weight of the absorbent polymer particles in the sections other than the sections folded inward of the absorbent pad sheet.

According to the first aspect, it is possible to prevent the leakage of the liquid excretions to the outside by absorbing plenty of the liquid excretions diffusing toward the width direction at the both ends of the absorbent pad and further, to prevent a gel blocking phenomenon by distributing the absorbent polymer particles within the front sheet because of the formation of the absorbent pad with absorbent polymer particles absorbing the liquid excretions that are provided in a liquid-permeable front sheet, in a liquid-permeable rear sheet and in between the liquid-permeable front sheet and the liquid-permeable rear sheet, the formation of the width in the width direction formed between the both ends folded inward 10 to 50% with respect to the width in the width direction of the absorbent pad and the passing of a part of the absorbent polymer particles in the sections folded inward to the inside of the front sheet in the sections folded inward. In addition, since pulp fibers are not used, the absorbent pad may be formed thin and it is possible to reduce the discomforts of the wearer.

According to the second aspect, in addition to the effect of the first aspect, it is possible to quickly diffuse the liquid excretions moved to the center of the width direction of the absorbent pad to the both ends of the absorbent pad because of the connection of the front sheet and the rear sheet with first junctions extending in the longitudinal direction at predetermined intervals in the width direction and second junctions extending in the width direction at predetermined intervals in the longitudinal direction and the packing of the absorbent polymer particles within plurality of cells defined by the first junctions and the second junctions when viewed in plan. In addition, it is possible to further prevent a gel blocking phenomenon of the absorbent polymer particles by controlling the uneven distribution of the absorbent polymer particles.

According to the third aspect, in addition to the effects of the first aspect or the second aspect, it is possible to adjust the passing amount of the absorbent polymer particles escaping into the front sheet in the sections folded inward at predetermined amount because of the formation of the base weight of the front sheet greater than the base weight of the rear sheet.

According to the fourth aspect, in addition to the effect of any one of the first, second, or third aspect, it is possible to adjust the passing amount of the absorbent polymer particles escaping into the front sheet in the sections folded inward at predetermined amount because of the formation of the thickness of the front sheet thicker than the thickness of the rear sheet.

According to the fifth aspect, in addition to the effects of any one of the first, second, third or fourth aspect, it is possible to prevent the leakage of the liquid excretions to the outside by absorbing even more of the liquid excretions diffusing toward the width direction at the both ends of the absorbent pad because of the arrangement the base weight of the absorbent polymer particles in the sections folded inward greater than the base weight of the absorbent polymer particles in the sections other than the sections folded inward of the absorbent pad sheet.

DETAILED DESCRIPTION

<Disposable Diapers>

The invention disclosing an absorbent pad with the excellent fluids diffusion and the excellent liquid permeability is described while referring to the figures. As used herein, the term "the longitudinal direction" refers to the direction connecting the stomach side and the back side, the term "the width direction" refers to the direction perpendicular to the longitudinal direction, the term "vertical direction" refers to the direction perpendicular to the waistline direction of disposable diapers in a worn state, the term "inner surface" refers to the body side of each parts respectively, and the term "outer surface" refers to the non-body side of each parts respectively.

Figure 1:
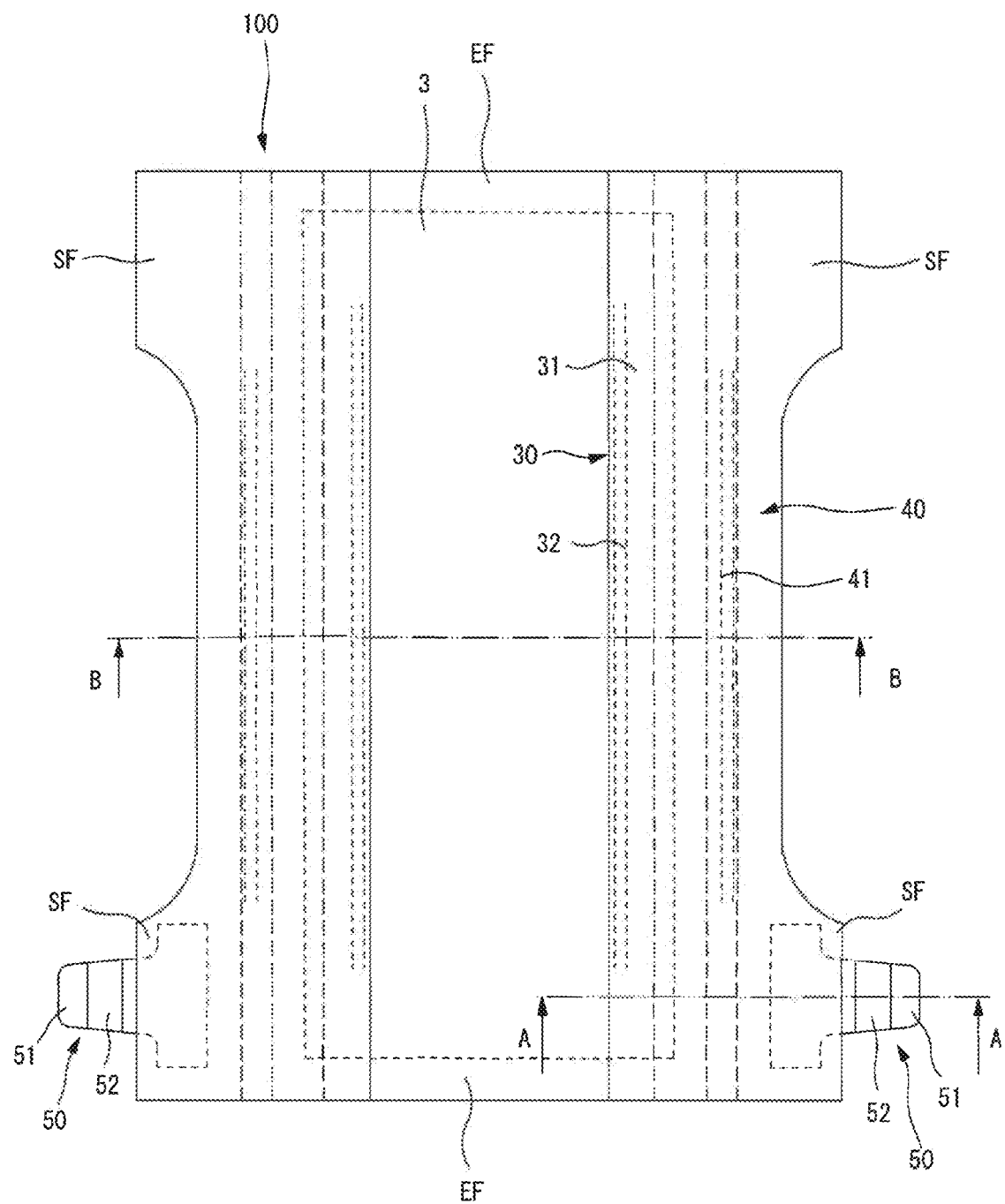
FIG. 1 is an expansion diagram showing the inner surface plan view of the disposable diapers.
Figure 2:
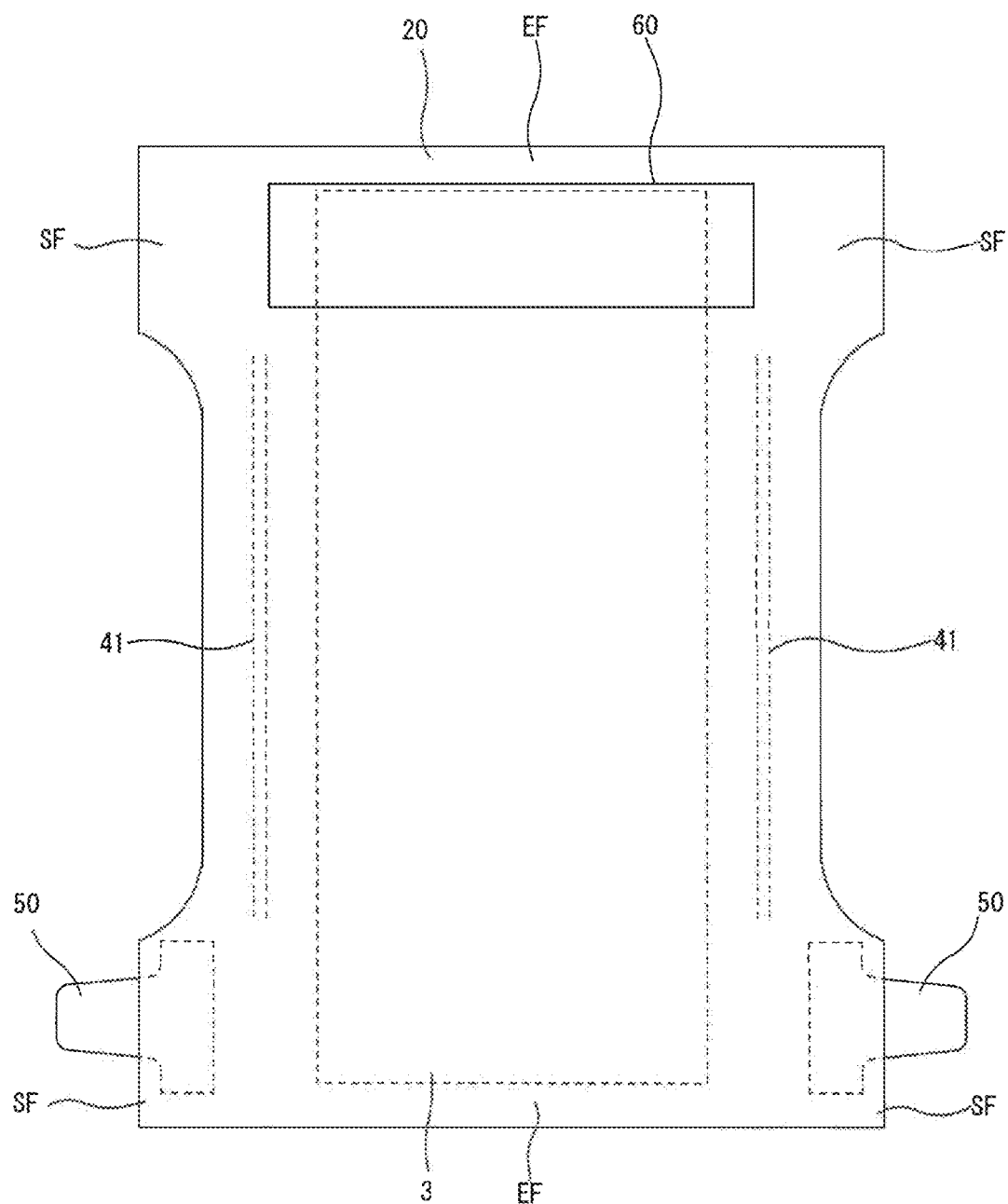
FIG. 2 is an expansion diagram showing the outer surface plan view of the disposable diapers.

As shown in FIGS. 1 and 2, the disposable diaper 100 comprises a liquid-permeable top sheet 1 on the body side, a liquid-impermeable back sheet 2 on the non-body side and the absorbent pad 3 positioned in between the top sheet 1 and the back sheet 2. Further, the exterior sheet 20 is used for the outer surface of the back sheet 2.

The three-dimensional gather 30 for the leg circumference is used for the outside of the absorbent pad 3 in the width direction respectively to prevent the leakage of the liquid excretions to outside, and the flat gather 40 for the leg circumference preventing the leakage of the liquid excretions to outside is used for the outside of the three-dimensional gather 30 respectively.

End flaps EF, where the absorbent pad 3 does not extend, is used for the outside of the absorbent pad 3 in the longitudinal direction respectively, and side flaps SF, where the absorbent pad 3 does not extend, is used for the outside of the absorbent pad 3 in the width direction respectively.

The fastening tapes 50 extending outward in the width direction is used for the back of the side flaps part SF respectively, and a target sheet 60 locking the fastening tapes 50 when wearing the disposable diaper 100 is used for the stomach side of the outer surface of the exterior sheet 20.

(Top Sheet)

The top sheet 1 extends more outward than the peripheral line of the absorbent pad 3, and the outer surface of the extending part is fixed to the inner surface of the back sheet 2 through an adhesive agent such as a hot melt.

Porous or nonporous non-woven fabric or perforated plastic sheet may be used for the top sheet 1. For the material fibers constituting the non-woven fabric, olefins such as polyethylene or polypropylene, polyesters, synthetic fibers such as amide-based, and others including regenerated fibers such as rayon or cupra as well as natural fibers such as cotton may be used. Further, as for the methods of non-woven fabric processes, the known methods such as a spun lace method, a spun bond method, a SMS method, a thermal bond method, a melt-blown method, a needle punching method, an air-through method, and a point bond method may be used. A fiber base weight of the non-woven fabric used for the top sheet 1 is preferably 15 to 30 $g/m^2$ and the thickness is preferably 0.05 to 1 mm.

(Back Sheet)

The back sheet 2 extends more outward than the peripheral line of the absorbent pad 3 and blocks the movement of the liquid excretions absorbed to the absorbent pad 3 to outside.

The back sheet 2, in addition to plastic films such as polyethylene films, may be moisture permeable sheets while keeping the water impermeable property from the viewpoint of the stuffiness prevention may be used. Microporous sheets obtained by stretching toward the uniaxial or biaxial direction after forming the sheets by melting and kneading inorganic fillers in olefin-based resins such as polyethylene or polypropylene may be used for the sheets with the water barrier property and the moisture permeability, for example. A base weight per unit area of the back sheet 2 is preferably 13 to 40 $g/m^2$ and the thickness is preferably 0.01 to 0.1 mm.

(Absorbent Pad)

Figure 3:
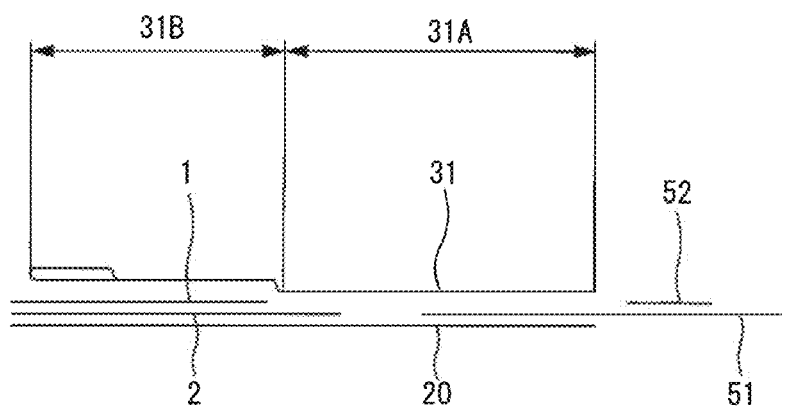
FIG. 3 is a cross sectional diagram showing A-A in FIG. 1.
Figure 4:
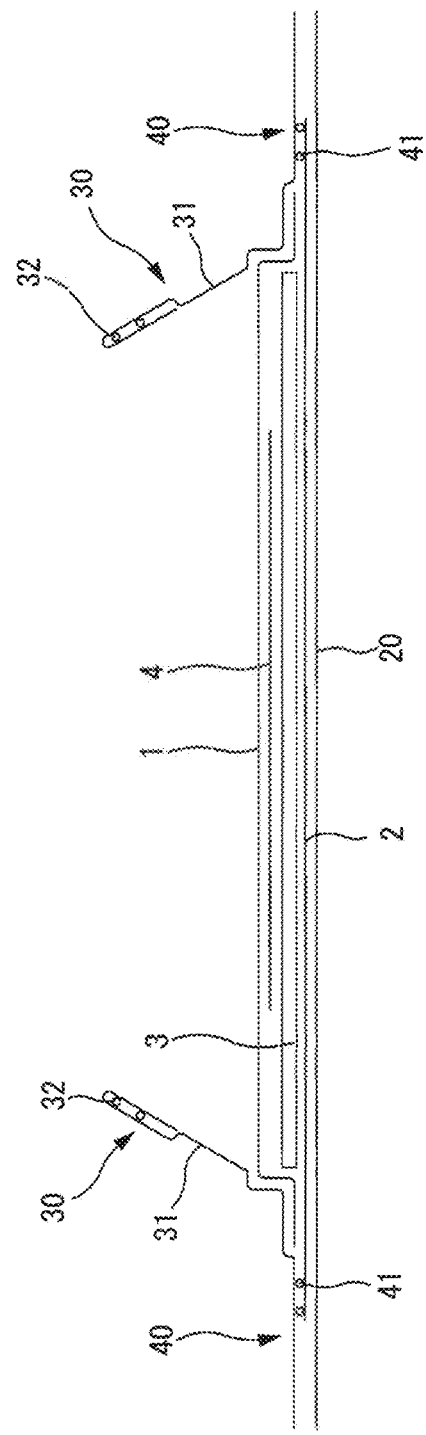
FIG. 4 is a cross sectional diagram showing B-B in FIG. 1.
Figure 7:
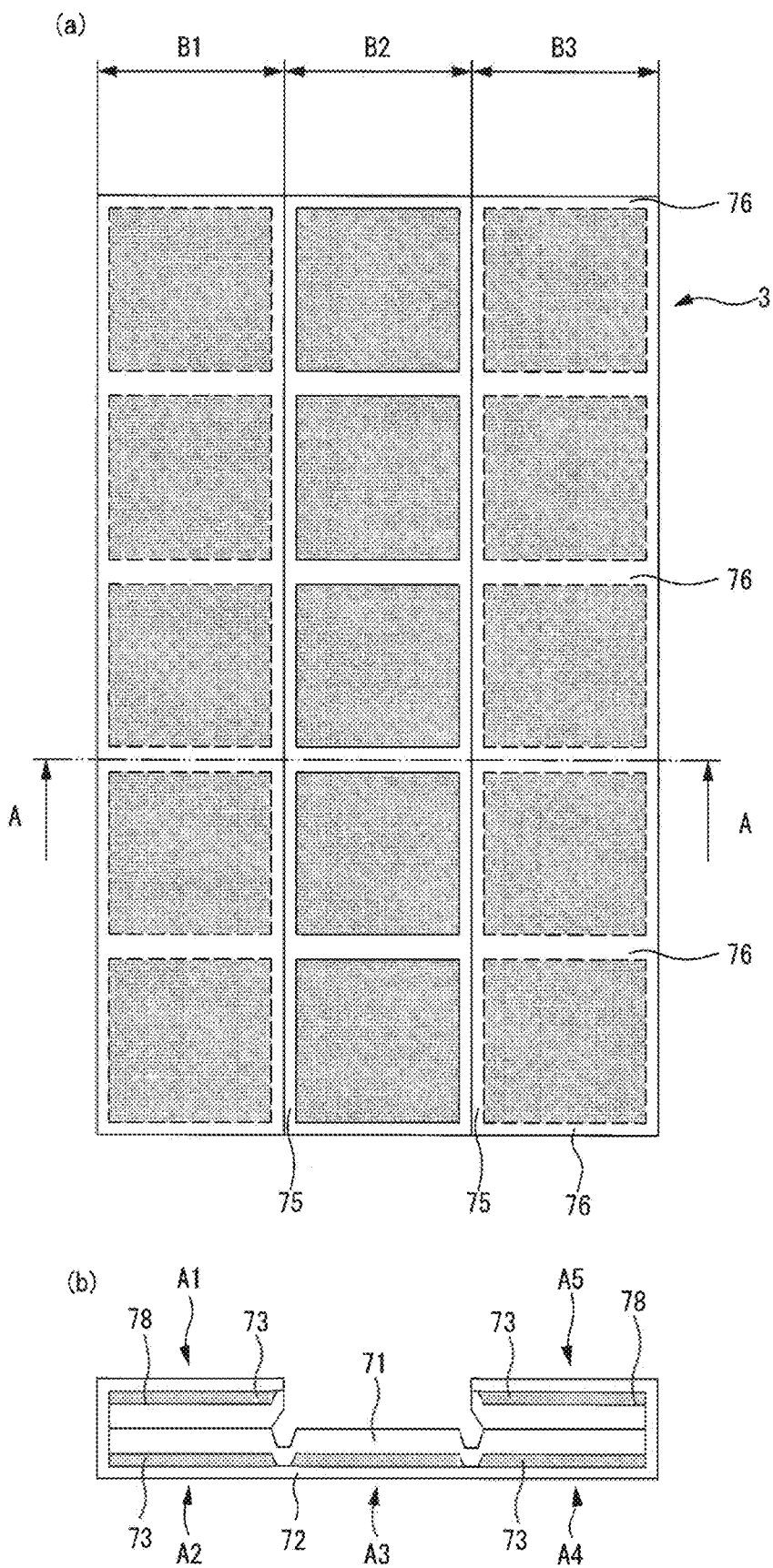
FIG. 7 is diagrams showing the absorbent pad of the first embodiment and (a) shows the inner surface plan view and (b) shows a cross sectional diagram of A-A.

As shown in FIGS. 3, 4 and 7, the absorbent pad 3 is formed by folding the front sheet 71 of the left folded section A1 of the absorbent pad sheet 70 toward the inside in the width direction as it counters to the front sheet 71 of the left section A2 and by folding the front sheet 71 of the right folded section A5 of the absorbent pad sheet 70 toward the inside in the width direction as it counters to the front sheet 71 of the right section A2. It is noted that the absorbent pad sheet 70 will be described later.

(Exterior Sheet)

The exterior sheet 20 is a sheet that covers the outer surface of the back sheet 2 and has a fabric-like appearance and texture for the outer surface of the disposable diaper 100. The exterior sheet is preferably formed with non-woven fabric. As for the material fibers, olefins such as polyethylene or polypropylene, polyesters, synthetic fibers such as amide-based, and others including regenerated fibers such as rayon or cupra as well as natural fibers such as cotton may be used and as for the processes, the methods such as a spun lace method, a spun bond method, a thermal bond method, an air-through method and a needle punching method may be used for the production. However, in the viewpoint of establishing compatibility between texture and strength, long fiber non-woven fabric such as spun bond non-woven fabric, SMS non-woven fabric or SMMS non-woven fabric is preferred.

In addition to the use of non-woven fabric in one piece, it is possible to use overlapping multiple sheets, and fixing the non-woven fabric by applying an adhesive agent such as a hot melt is preferred when using overlapping multiple sheets. Further, the fiber base weight is preferably 10 to 50 g/m$^2$, especially 15 to 30 g/m$^2$ is preferred when using a non-woven fabric.

(Three-Dimensional Gather for the Leg Circumference)

The outer surface of a base 31A of the gather sheet 31 forming the three-dimensional gather 30 for the leg circumference is fixed to the outside of the inner part of the back sheet 2 in the width direction and the outside of the inner part of the exterior sheet 20 in the width direction respectively throughout the longitudinal direction. Further, the both ends of raised portions 31B of the gather sheet 31 in the longitudinal direction are fixed to the outside of the inner part of the top sheet 1 in the width direction, and the middle part of the raised portions 31B of the gather sheet 31 in the longitudinal direction is not fixed to the inner part of the top sheet 1 but separated.

The plurality of elongated elastic stretchable strips 32 with the predetermined extension shape extending in the longitudinal direction at the predetermined intervals in the width direction are provided to the raised portions 31B of the gather sheet 31. Accordingly, when wearing the disposable diaper 100, the raised portions 31B is raised toward the crotch part of the wearer by the shrinkage force of the elastic stretchable strips 32, and the leakage of the liquid excretions to outside can be prevented by pressing and contacting the tip of the raised portions 31 against the crotch part of the wearer.

The gather sheet 31, in addition to the non-woven fabric such as spun bond non-woven fabric, may be the plastic films similar to the ones used for the back sheet 2 and those laminated sheets may be used, however, in the viewpoint of establishing the feeling of the skin, non-woven fabric performed water repellent treatment is preferred.

For the elastic stretchable strips 32, regular materials such as thread-like, string-like and belt-like natural rubbers or synthetic rubbers, specifically styrene-based rubbers, olefin rubbers, urethane rubbers, ester-based rubbers, polyurethanes, polyethylenes, polystyrenes, styrene-butadienes, silicons and polyesters may be used. Further, the thickness of the elastic stretchable strips 32 is approximately 500 to 1500 dtex, especially around 800 to 1300 dtex (in case of natural rubbers, approximately 0.1 to 3 mm, especially around 0.5 to 3 mm) is preferred, and the elongation percentage at the time of installation is approximately 150 to 250%, especially around 160 to 200% is preferred.

(Flat Gather for the Leg Circumference)

The flat gather 40 for the leg circumference is provided to the base 31A of the gather sheet 31 forming the three-dimensional gather 30. The elongated elastic stretchable strips 41 with the predetermined extension shape extending in the longitudinal direction at the predetermined intervals in the width direction are provided to the base 31A of the gather sheet 31 forming the side flaps part SF and the outside of the back sheet 2 in the width direction. Accordingly, when wearing the disposable diaper 100, the flat gather 40 is pressing and contacting to the crotch part of the wearer by the shrinkage force of the elastic stretchable strips 41, and the leakage of the liquid excretions to outside can be prevented.

For the elastic stretchable strips 41, regular materials such as thread-like, string-like and belt-like natural rubbers or synthetic rubbers, specifically styrene-based rubbers, olefin rubbers, urethane rubbers, ester-based rubbers, polyurethanes, polyethylenes, polystyrenes, styrene-butadienes, silicons and polyesters may be used. In addition, the spacing between the elastic stretchable strips 41 is approximately 2 to 15 mm, especially around 3 to 7 mm is preferred. Further, the thickness of the elastic stretchable strips 41 is approximately 500 to 1500 dtex, especially around 800 to 1300 dtex (in case of natural rubbers, approximately 0.1 to 3 mm, especially around 0.5 to 3 mm) is preferred, and the elongation percentage at the time of installation is approximately 150 to 250%, especially around 160 to 200% is preferred.

(Fastening Tape)

As shown in FIGS. 1 to 3, the fastening tapes 50 extending toward outside is provided to the back of the side flaps part SF respectively. The fastening tapes 50 comprises the base sheet 51 and the locking section 52 provided to the outside of the inner surface of the base sheet 51. Further, the inner part of the base sheet 51 is fixed to the outside of the gather sheet 31 and the exterior sheet 20 in the width direction.

The non-woven fabric is preferred for the material of the base sheet 51 and any known non-woven fabric may be used without a particular limitation. For the material fibers constituting the non-woven fabric, olefins such as polyethylene or polypropylene, polyesters, synthetic fibers such as amide-based, and others including regenerated fibers such as rayon or cupra as well as natural fibers such as cotton may be used. Further, for the methods of non-woven fabric processes, the known methods such as a spun lace method, a spun bond method, a SMS method, a thermal bond method, a melt-blown method, a needle punching method, an air-through method, and a point bond method may be used. Especially, the spun bond non-woven fabric using olefin fibers and SMS non-woven fabric are preferred. Although the base weight of the non-woven fabric used may be appropriately determined, the total base weight of the non-woven fabric for the main unit 5b is 20 to 75 g/m$^2$, especially 26 to 46 g/m$^2$, and the total base weight of the non-woven fabric for the fixed part 5f and the tip part 5p is 35 to 130 g/m$^2$ respectively, especially 46 to 116 g/m$^2$, are preferred. Within this range, it is possible to ensure the strength and the rigidity of the base section fixed in between the exterior sheet 20 and the gather sheet 31, and further secure the flexibility and the elasticity of the main unit 74.

For the locking section 52, hook materials of a mechanical fastener are preferred. The hook materials may have multiple engaging protrusions. The configuration of the engaging protrusions may be in shapes such as (A) a mirror-inverted J shape, (B) J-shape, (C) mushroom-shape, (D) T-shape and (E) a dual J shape (a combination of two Js joined together back to back like a fishhook), but it may be in any shape. Alternatively, it is possible to use pressure-sensitive adhesive layers instead of the hook materials.

(Target Sheet)

For the target sheet 60, preferred materials are such as plastic films with plurality of loop yarn on the surface side and non-woven fabrics. Thus, when wearers wear the disposable diaper 100, it is possible to efficiently lock the locking section 52 of the fastening tapes 50 to the target sheet 60.

(Interlayer Sheet)

In the first embodiment, the interlayer sheet 4 is provided in between the top sheet 1 and the absorbent pad 3. Thus, the liquid excretions passing through the top sheet 1 can move quickly to the absorbent pad 3 and it is possible to prevent the liquid excretions from returning to the top sheet 1. It is noted that the interlayer sheet 4 is fixed to the outside of the top sheet 1 by a hot melt adhesive agent, heat embossing or ultrasonic wave welding.

For the interlayer sheet 4, in addition to the use of the non-woven fabrics, resin films with numerous permeation holes may be used. For the non-woven fabrics, the materials similar to the top sheet 1 may be used, however, the materials having higher hydrophilicity and fiber density than the top sheet 1 is preferred in order to have excellent movement properties of the liquid excretions from the top sheet 1 to the interlayer sheet 4.

<Absorbent Pad Sheet>

First Embodiment

Figure 5:
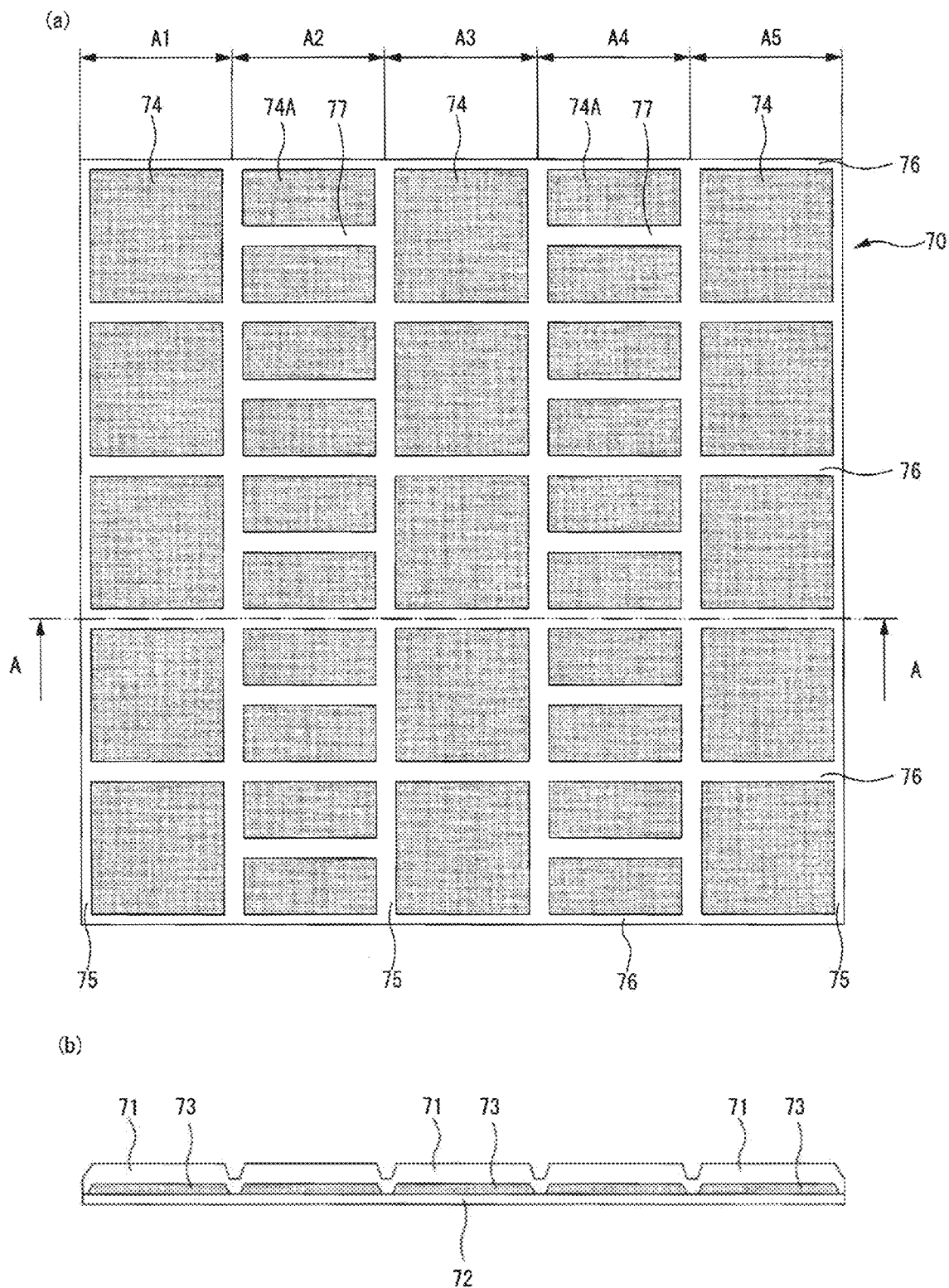
FIG. 5 is expansion diagrams showing the absorbent pad of the first embodiment and (a) shows the inner surface plan view and (b) shows a cross sectional diagram of A-A.

The absorbent pad sheet 70 in the first embodiment forming the absorbent pad 3 is described herein. As shown in FIG. 5, the absorbent pad sheet 70 is formed with the absorbent polymer particles 73 provided in the liquid-permeable front sheet 71 on the top sheet 1 side, in a liquid-permeable rear sheet 72 on the back sheet 2 side and in between the front sheet 71 and the rear sheet 72.

The front sheet 71 and the rear sheet 72 are connected by the junctions and the absorbent polymer particles 73 are used for plurality of the cells 74 defined by the junctions respectively. It is noted that the front sheet 71 and the rear sheet 72 positioned to the cells 74 are separated without connections and formed with predetermined spaces. Thus, it is possible to prevent the absorbent polymer particles 73 from being in one part of the absorbent pad sheet 70 and to control an occurrence of a gel blocking phenomenon. Further, in addition to being able to unbind the absorbent polymer particles 73 for the front sheet 71 or the rear sheet 72, it is possible to bond to the front sheet 71 or the rear sheet 72 by using a hot melt adhesive agent.

The junctions are formed with 6 of the junctions 75 ("First junctions" recited in claims) extending toward the longitudinal direction at the predetermined intervals in the width direction of the absorbent pad sheet 70 and 6 of the junctions 75 ("Second junctions" recited in claims extending toward the width direction at the predetermined intervals in the longitudinal direction of the absorbent pad sheet 70. As used herein, counting from left to right, the term "Left folded section A1" refers to the section defined by the first junctions of 75 and the second junctions of 75, the term "Left section A2" refers to the section defined by the second junctions of 75 and the third junctions of 75, the term "Center section A3" refers to the section defined by the third junctions of 75 and the fourth junctions of 75, the term "Right section A4" refers to the section defined by the fourth junctions of 75 and the fifth junctions of 75 and the term "Right folded section A5" refers to the section defined by the fifth junctions of 75 and the sixth junctions of 75.

When viewed in plan, the cells 74 formed in the left folded section A1 are configured in approximately squares, the cells 74 formed in the left section A2 are separated in the longitudinal direction by the junctions 77 extending in the width direction, and the separated small cells 74A are configured in approximately rectangles having the long side in the width direction. The cells 74 formed in the center section A3 are configured in approximately squares, the cells 74 formed in the right section A4 are separated in the longitudinal direction by the junctions 77 extending in the width direction, and the separated small cells 74A are configured in approximately rectangles having the long side in the width direction. The cells 74 formed in the right folded section A5 are configured in approximately squares.

Porous or nonporous non-woven fabric may be used for the front sheet 71. When using a non-woven fabric, use of a non-woven fabric produced by an air-through method, a melt-blown method or a needle punching method is preferred, and further, it is preferred to make the fiber diameter of the non-woven fabric used for the front sheet 71 thicker than the fiber diameter used for the rear sheet 72, to make the fiber base weight of the non-woven fabric of the front sheet 71 greater than the fiber base weight of the non-woven fabric used for the rear sheet 72 and to make the thickness of the non-woven fabric of the front sheet 71 thicker than the thickness of the non-woven fabric used for the rear sheet 72. Therefore, it is possible to efficiently absorb the liquid excretions diffusing toward the width direction since the predetermined amount of the absorbent polymer particles 73 provided to the cells 74 within the left folded section A1 folded inward to the left section A2 of the absorbent pad sheet 70 is transferred. Similarly, it is possible to efficiently absorb the liquid excretions diffusing toward the width direction since the predetermined amount of the absorbent polymer particles 73 provided to the cells 74 within the right folded section A5 folded inward to the right section A4 of the absorbent pad sheet 70 is transferred. In addition, the fiber diameter of the non-woven fabric used for the front sheet 71 is preferably 3.0 to 30 dtex, the fiber base weight is preferably 20 to 100 g/m$^2$ and the thickness is preferably 2 to 5 mm.

Porous or nonporous non-woven fabric may be used for the rear sheet 72. When using a non-woven fabric, use of a high fiber density non-woven fabric produced by a spun bond method, a melt-blown method or a needle punching method is preferred, and therefore, it is possible to minimize the escape of the absorbent polymer particles 73 from the cells 74. In addition, the fiber diameter of the non-woven fabric used for the rear sheet 72 is preferably 1.0 to 3.0 dtex, the fiber base weight is preferably 10 to 20 g/m$^2$ and the thickness is preferably 0.2 to 2 mm.

The high absorbent polymer particles used for absorption items such as disposable diapers and sanitary napkins may be used for the absorbent polymer particles 73. The high absorbent polymer particles may be starch, cellulose and synthetic polymers, and starch-acrylic acid (salt) graft copolymer, saponified product of starch—acrylonitrile copolymer, crosslinked products of sodium carboxymethylcellulose and acrylic acid (salt) polymer.

The water absorption of the absorbent polymer particles 73 is preferably more than 40 g/g and the water absorption rate is preferably less than 70 seconds, especially less than 40 seconds. Accordingly, it is possible to efficiently absorb the liquid excretions passing through the Top Sheet 1 with the absorbent pad sheet 70 and to prevent the liquid excretions from returning to the Top Sheet 1.

The gel strength of the absorbent polymer particles 73 is preferably more than 1,000 Pa. Accordingly, it is possible to reduce the stickiness of the absorbent pad sheet 70 absorbing the liquid excretions.

The particle diameter of the absorbent polymer particles 73 is preferably, when sifting (shaking for 5 minutes) by using a 500 μm standard sieve (JISZ8801-1:2006) and sifting (shaking for 5 minutes) the particles falling under the sieve with the sifting by using a 180 μm standard sieve (JISZ8801-1:2006), such that the ratio of the particles remaining on the 500 μm standard sieve is less than 30 wt. % and the ratio of the particles remaining on the 180 μm standard sieve is more than 60 wt. %.

The fiber base weight of the absorbent polymer particles 73 of the cells 74, although determined appropriately depending on the absorption amount required, is preferably 50 to 350 g/m². Further, ensuring the absorption amount becomes difficult if the fiber base weight is less than 50 g/m² and the absorption amount becomes too excessive if the fiber base weight is more than 350 g/m². In addition, the configuration of the cells 74 is formed in squares in the plan view, however, shapes of rectangles, rhombus, hexagon, circle, and ellipse can be formed as well. Furthermore, when the cells 74 are formed in hexagonal shapes, the junctions 75 are formed extending in the longitudinal direction while being uneven in the width direction along the shapes of hexagons in the width direction, and the junctions 76 are formed extending in the width direction while being uneven in the longitudinal direction along the shapes of hexagons in the longitudinal direction.

The width in the width direction of the junctions 75 is formed in 5 to 10 mm, the width in the longitudinal direction of the junctions 76 is formed in 5 to 10 mm and the width in the longitudinal direction of the junctions 77 is formed in 5 to 10 mm. Therefore, the liquid excretions passing through the top sheet 1 can be spread throughout the entire absorbent pad sheet 70 and the liquid excretions can be absorbed efficiently with the plurality of cells 74.

The junctions 75, the junctions 76 and the junctions 77 are preferably bonded by welding the front sheet 71 and the rear sheet 72 similar to ultrasonic wave welding or heat sealing, however, a hot melt adhesive agent may be used for bonding.

Figure 6:
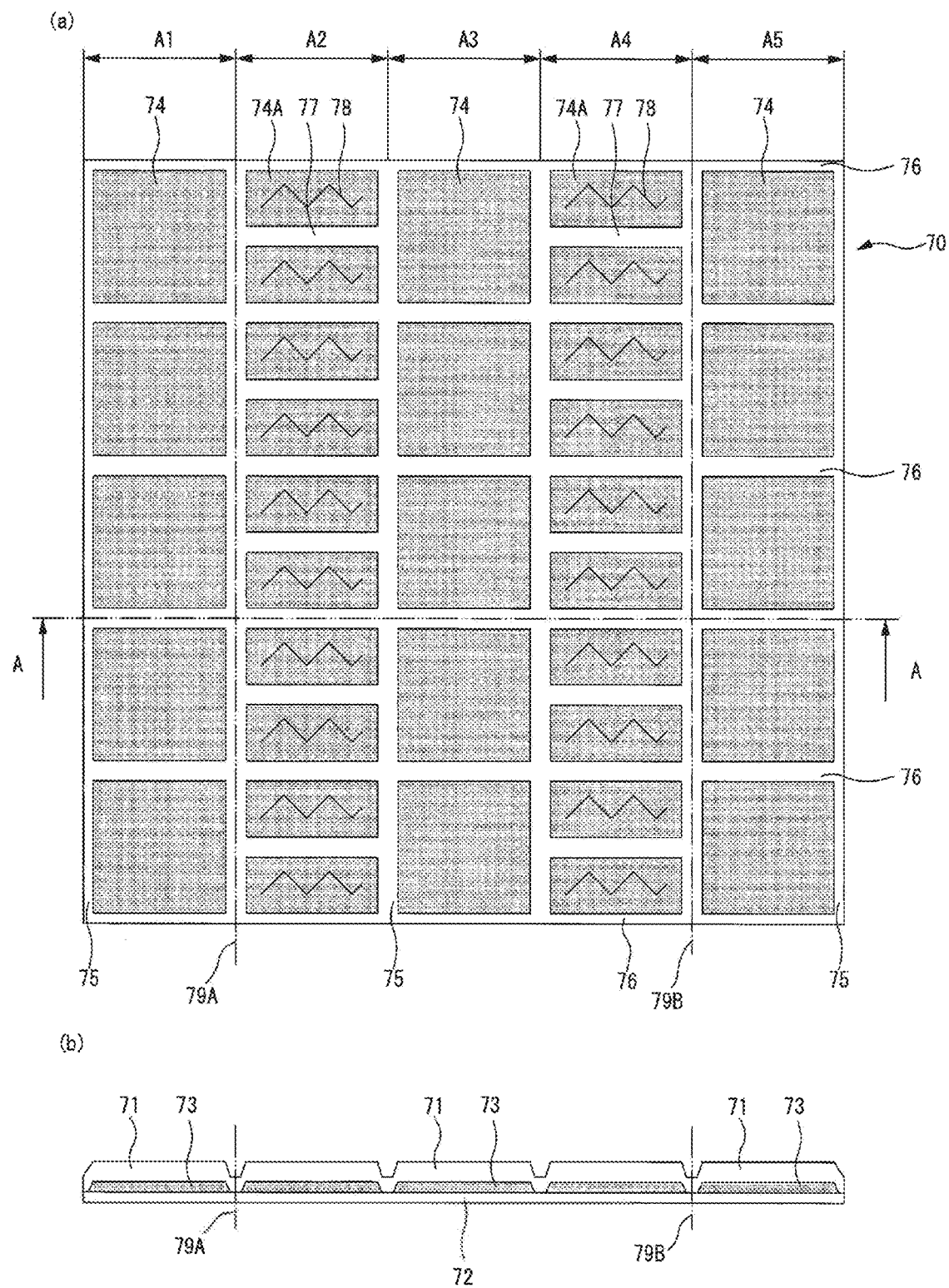
FIG. 6 is expansion diagrams showing the absorbent pad of the first embodiment right before folding and (a) shows the inner surface plan view and (b) shows a cross sectional diagram of A-A.

Next, a technique forming the absorbent pad 3 by folding the absorbent pad sheet 70 is described. As shown in FIG. 6, first, the hot melt adhesive agent 78 is applied to the front sheet 71 positioned in the left section A2 and the right section A4 of the absorbent pad sheet 70. It is noted that the hot melt adhesive agent 78 is preferably applied in the spiral shape or the striped shape in order to maintain a high liquid permeability.

Next, having the folding line 79A extending toward the longitudinal direction where approximately the center in the width direction of junctions 75 in between the left folded section A1 and the left section A2 as the center, fold the left folded section A1 inward, and bond the front sheet 71 positioned to the left folded section A1 and the front sheet 71 positioned to the left section A2 by applying the hot melt adhesive agent 78. Similarly, having the folding line 79B extending toward the longitudinal direction where approximately the center in the width direction of junctions 75 in between the right folded section A5 and the right section A4 as the center, fold the right folded section A5 inward, and bond the front sheet 71 positioned to the right folded section A5 and the front sheet 71 positioned to the right section A4 by applying the hot melt adhesive agent 78. It is noted that, instead of the hot melt adhesive agent 78, a thermocompression bonding or an ultrasonic wave welding may be used to bond the left folded section A1 with the left section A2 and the right folded section A5 with the right section A4.

Next, the absorbent pad 3 formed by folding the absorbent pad sheet 70 is described. As shown in FIG. 7, the left section B1 and the right section B3 of the absorbent pad 3 in the width direction are formed in a convex configuration toward more inside (the body side) than the center section B2 of the absorbent pad 3 in the width direction. Thus, it is possible to reduce the discomforts of the wearer by preventing the liquid excretions (hereinafter referred to the excess liquid excretions) not absorbed to the center section B2 of the absorbent pad 3 from contacting the wearer such as buttocks.

The width of the center section B2 of the absorbent pad 3 in the width direction is preferably 10 to 40% with respect to the width of the absorbent pad 3 in the width direction. There is a risk of the transfer of the liquid excretions passing through the top sheet 1 to the left section B1 or the right section B3 of the absorbent pad 3 if the width of the center section B2 is less than 10%. Further, there is a risk of not being able to absorb all the excess liquid excretions diffused in the width direction if the width of the center section B2 is more than 40%.

The junctions 76 extending toward the width direction are formed to the left section B1 and the right section B3 of the absorbent pad 3. Therefore, it is possible to quickly diffuse the excess liquid excretions to the left section B1 and the right section B3 of the absorbent pad 3 and to control an occurrence of a gel blocking phenomenon. In addition, the junctions 77 extending toward the width direction are further formed to the left section A2 forming the outside (non-body side) of the left section B1 and the right section A4 forming the outside of the right section B3 of the absorbent pad 3. Thus, it is possible to more quickly diffuse plenty of the excess liquid excretions to the left section B1 and the right section B3 of the absorbent pad 3 by the junctions 76 and the junctions 77, making the absorption rate faster, and to prevent the leakage to the outside. Furthermore, it is possible to reduce the discomforts of the wearer by reducing the rewetting incident because the excess liquid excretions diffusing to the left section B1 of the absorbent pad 3 are absorbed to the left folded section A1 and the left section A2 forming the left section B1, and the excess liquid excretions diffusing to the right section B3 of the absorbent pad 3 are absorbed to the right folded section A5 and the right section A4 forming the right section B3.

Figure 8:
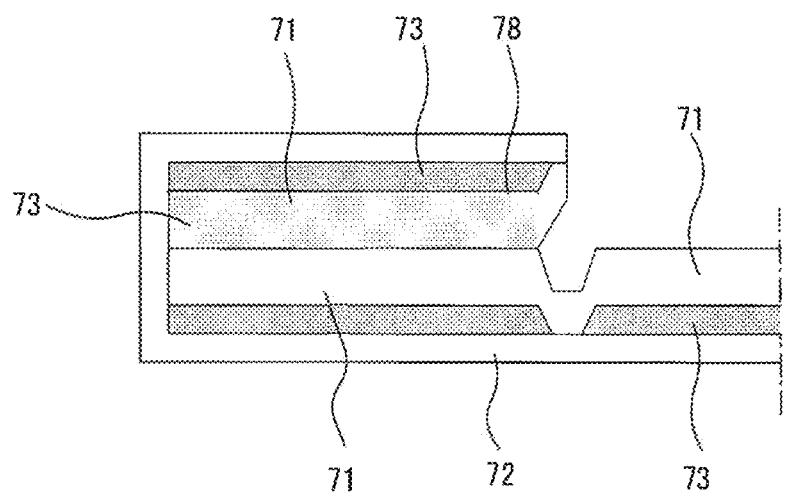
FIG. 8 is an explanatory diagram showing the left side of the folded absorbent pad of the first embodiment.

As shown in FIG. 8, the absorbent polymer particles 73 escaped from the cells 74 are distributed to the left folded section A1 of the front sheet 71 forming the left section B1 and the right folded section A5 of the front sheet 71 forming the right section B3 of the absorbent pad 3. Thus, it is possible to prevent the leakage to the outside by absorbing the excess liquid excretions diffusing to the left section B1 and the right section B3 of the absorbent pad 3.

Second Embodiment

Figure 9:
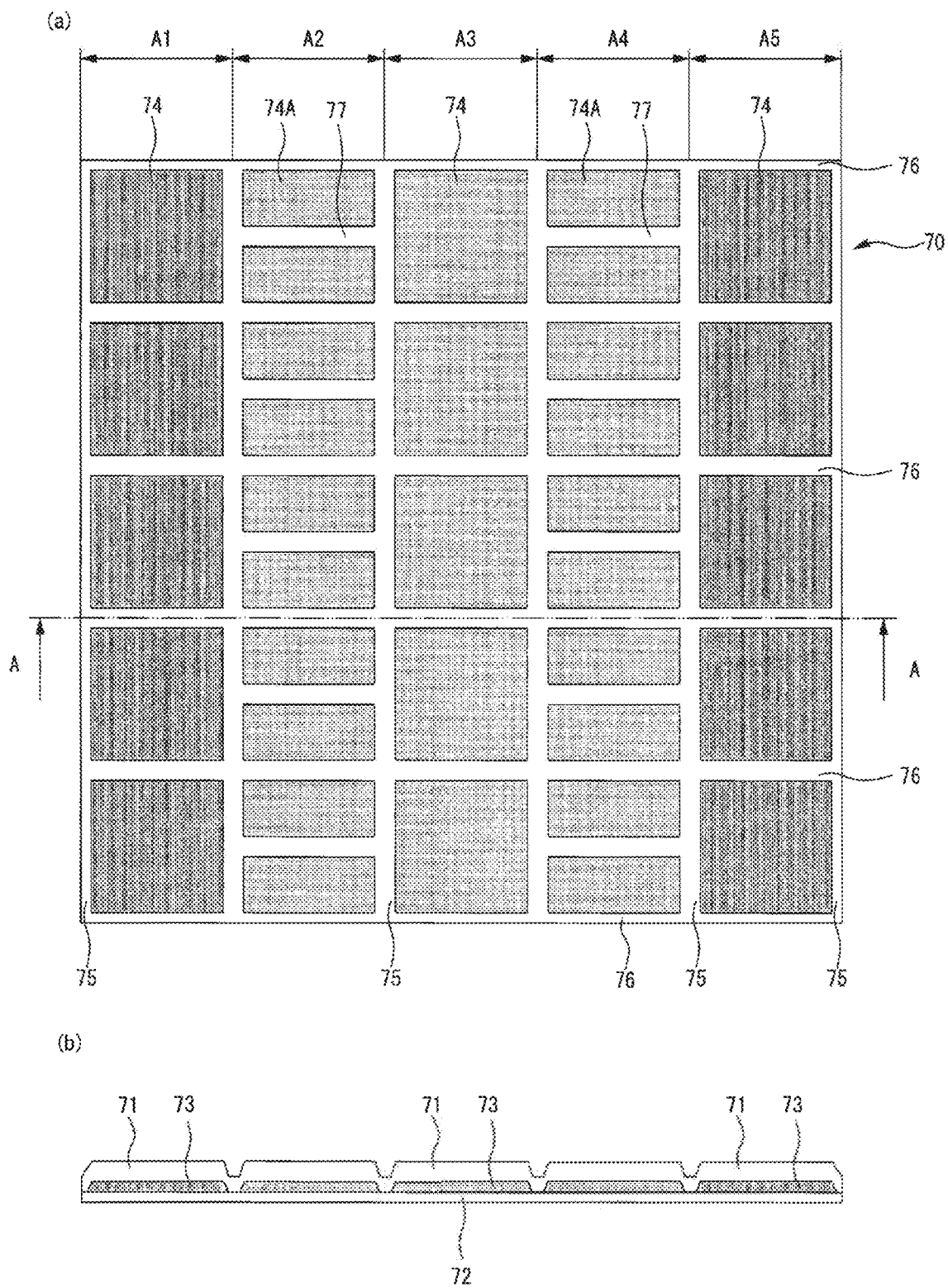
FIG. 9 is expansion diagrams showing the absorbent pad of the second embodiment right before folding and (a) shows the inner surface plan view and (b) shows a cross sectional diagram of A-A.

The absorbent pad sheet 70 of the second embodiment forming the absorbent pad 3 is described. It is noted that the same members as the absorbent pad sheet 70 in the first embodiment are described with the same reference numerals and the explanations are not repeated. As shown in FIG. 9, in the absorbent pad sheet 70 of the second embodiment, the base weight of the absorbent polymer particles 73 provided to the cells 74 formed to the left folded section A1 and the right folded section A5 of the absorbent pad sheet 70 is set to 150% with respect to the base weight of the absorbent polymer particles 73 provided to the cells 74 formed to the left section A2, the center section A3 and the right section A4 of the absorbent pad sheet 70. It is noted that the base weight of the absorbent polymer particles 73 is differentiated in the absorbent pad sheet 70 of the second embodiment, however, a material, amount of the liquid absorption, a gel strength or a particle size of the absorbent polymer particles 73 may be differentiated as well.

Figure 10:
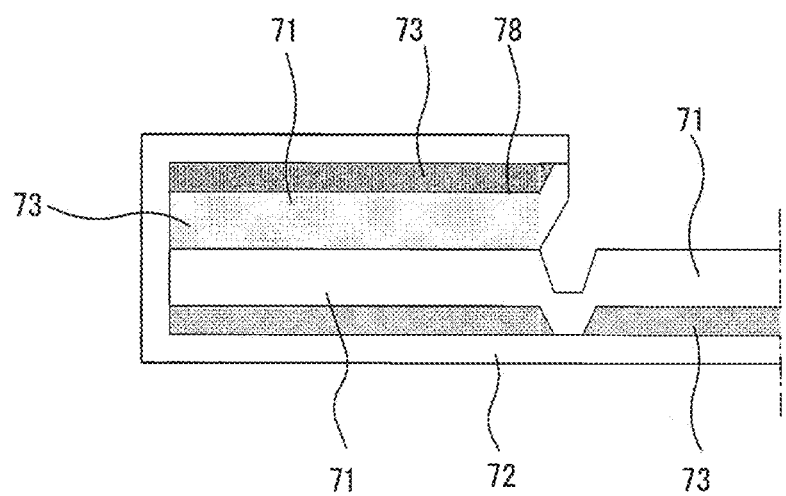
FIG. 10 is an explanatory diagram showing the left side of the folded absorbent pad of the second embodiment.

As shown in FIG. 10, plenty of absorbent polymer particles 73 escaped from the cells 74 are distributed to the left folded section A1 of the front sheet 71 forming the left section B1 and the right folded section A5 of the front sheet 71 forming the right section B3 of the absorbent pad 3 formed by folding the absorbent pad sheet 70 of the second embodiment. Thus, it is possible to prevent the leakage to the outside by absorbing more excess liquid excretions diffusing to the left section B1 and the right section B3 of the absorbent pad 3.

Other Folding Embodiment

Figure 11:
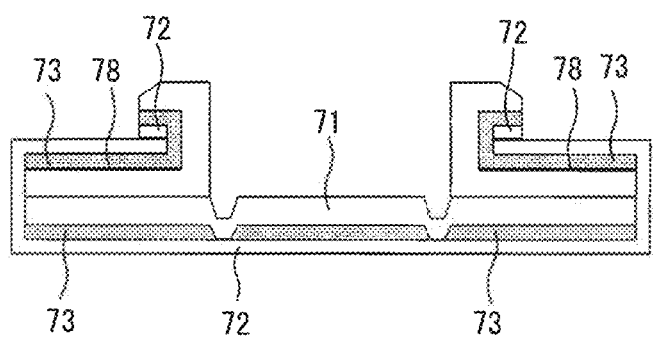
FIG. 11 is a diagram showing other folding embodiment.

Next, the other folding embodiment is described. It is noted that the same components as the absorbent pad sheet 70 in the first embodiment are described with the same reference numerals and the explanations are not repeated. As shown in FIG. 11, the inside part in the width direction of the left folded section A1 forming the left section B1 of the absorbent pad 3 may be folded outward and the inside part in the width direction of the right folded section A5 forming the right section B3 of the absorbent pad 3 may be folded outward. Thus, it is possible to reduce even more discomforts of the wearer by preventing more liquid excretions from contacting the wearer such as buttocks.

The present invention is available for absorbent articles such as tape type disposable diapers, pants type disposable diapers and sanitary napkins and pads.

The invention claimed is:

1. An absorbent pad comprising:
an absorbent pad formed by folding the both ends of the width direction of an absorbent pad sheet inward wherein:
the absorbent pad sheet is formed with a liquid-permeable front sheet, a liquid-permeable rear sheet and absorbent polymer particles absorbing the liquid excretions that are provided in between the liquid-permeable front sheet and the liquid-permeable rear sheet;
a width in the width direction formed between the both ends folded inward is formed 10~50% with respect to a width in the width direction of the absorbent pad; and
a part of the absorbent polymer particles in the sections folded inward is passed through the front sheet in the sections folded inward;
wherein, when viewed in plan, the front sheet and the rear sheet are connected by a plurality of junctions; and the absorbent polymer particles are packed within a plurality of cells defined by the junctions.

2. The absorbent pad of claim 1, wherein the junctions include first junctions extending in the longitudinal direction at predetermined intervals in the width direction and second junctions extending in the width direction at predetermined intervals in the longitudinal direction.

3. The absorbent pad of claim 1, wherein the base weight of the front sheet is formed greater than the base weight of the rear sheet.

4. The absorbent pad of claim 3, wherein the thickness of the front sheet is formed thicker than the thickness of the rear sheet.

5. The absorbent pad of claim 3, wherein the base weight of the absorbent polymer particles in the sections folded inward is arranged greater than the base weight of the absorbent polymer particles in the sections other than the sections folded inward of the absorbent pad sheet.

6. The absorbent pad of claim 1, wherein the thickness of the front sheet is formed thicker than the thickness of the rear sheet.

7. The absorbent pad of claim 6, wherein the base weight of the absorbent polymer particles in the sections folded inward is arranged greater than the base weight of the absorbent polymer particles in the sections other than the sections folded inward of the absorbent pad sheet.

8. The absorbent pad of claim 1, wherein the base weight of the absorbent polymer particles in the sections folded inward is arranged greater than the base weight of the absorbent polymer particles in the sections other than the sections folded inward of the absorbent pad sheet.

9. The absorbent pad of claim 1, wherein the base weight of the front sheet is formed greater than the base weight of the rear sheet.

10. The absorbent pad of claim 1, wherein the thickness of the front sheet is formed thicker than the thickness of the rear sheet.

11. The absorbent pad of claim 1, wherein the base weight of the absorbent polymer particles in the sections folded inward is arranged greater than the base weight of the absorbent polymer particles in the sections other than the sections folded inward of the absorbent pad sheet.

* * * * *